United States Patent [19]
West et al.

[11] Patent Number: 6,062,429
[45] Date of Patent: May 16, 2000

[54] APPARATUS FOR SUPPORTING AND DISCHARGING FLEXIBLE FLUID CONTAINERS

[75] Inventors: Joe E. West; Garrett L. Barker, both of Meridian, Tex.

[73] Assignee: Valley West, Inc., Meridian, Tex.

[21] Appl. No.: 09/146,305

[22] Filed: Sep. 3, 1998

[51] Int. Cl.[7] ........................................................ B65B 1/04
[52] U.S. Cl. ...................... 222/95; 604/141; 129/DIG. 12
[58] Field of Search ................................ 222/95, 96, 105, 222/106; 604/141, 146, 147; 128/DIG. 12

[56] References Cited

U.S. PATENT DOCUMENTS

| | | |
|---|---|---|
| 3,895,741 | 7/1975 | Nugent . |
| 4,539,005 | 9/1985 | Greenblatt . |
| 5,720,728 | 2/1998 | Ford . |

*Primary Examiner*—Steven O. Douglas
*Attorney, Agent, or Firm*—Akin, Gump, Strauss, Hauer & Feld, L.L.P.

[57] ABSTRACT

An apparatus for supporting and forcibly discharging flexible irrigation fluid bags under controlled pressure includes a body having a recess formed therein slightly inclined to the vertical and cooperating with brackets at the lower end of the recess to support and retain a bag therein and wherein the bag discharge conduits depend from the body between the brackets. A door is hinged to the body and movable to a closed position for engaging the bag during forcible deflection of the bag to discharge fluid therefrom. An inflatable bladder is supported in the recess in the body and is connected to a source of pressure air at a cylindrical ported plug and providing for disconnection of the bladder from the plug in response to an overpressure condition. Pressure air is supplied to the inflatable bladder by way of a control circuit including a rapid opening high volume air supply and exhaust valve for quickly venting the inflation chamber.

24 Claims, 6 Drawing Sheets

APPARATUS FOR SUPPORTING AND DISCHARGING FLEXIBLE FLUID CONTAINERS

FIELD OF THE INVENTION

The present invention pertains to an apparatus for supporting a flexible bag fluid container, such as a medical procedure irrigation fluid bag, and for exercising controlled squeezing of the bag to discharge fluid therefrom at a controlled rate.

BACKGROUND

In administering irrigation fluids from flexible bag containers during certain medical procedures it is desirable to provide container support apparatus which is operable to also be capable of exerting a pressure force on the fluid container to discharge fluid therefrom at a rate other than that which is available as a consequence of hydrostatic pressure, since this pressure will vary depending upon the position of the bag relative to the point of injection of the fluid and the quantity of fluid remaining in the bag. In this regard apparatus has been developed which is operable to squeeze the fluid container to force the discharge of fluids therefrom.

However, heretofore apparatus for performing the function described above has been lacking certain desired improvements. In particular, prior art apparatus for supporting flexible fluid containers has not been adapted to handle containers of various sizes. The containers are supported on the apparatus by hanging the containers from a point near the top end of the container and the container discharge ports are then often pinched by the apparatus closure or do not extend below the bottom of the support structure for easy access. In other words, known apparatus has not been adapted to accommodate fluid containers of different lengths and overall sizes and fabricated by different manufacturers.

Another problem associated with prior art apparatus for supporting flexible fluid containers is the lack of ability to retain the fluid container in a suitable working position when the apparatus door or closure is open and to remain in the working position until the container is forcibly grasped to remove it from its support structure. Still further, prior art fluid actuated container discharge devices have not been adapted to quickly relieve pressure forces acting on the fluid container to reduce or cease discharge of fluid therefrom. Still further, there has been a desire to provide improved operation of flexible fluid container discharge or infusion devices and to control the operating mode of such devices. These improvements and certain other improvements in the art of apparatus for supporting and discharging flexible fluid containers for use in medical procedures, in particular, have been met by the present invention.

SUMMARY OF THE INVENTION

The present invention provides an improved apparatus for supporting flexible fluid containers, particularly irrigation fluid containers or "bags" of different lengths and sizes, and for exerting a pressure force or squeezing action on such containers to control the discharge of fluid therefrom.

In accordance with one aspect of the present invention an apparatus is provided for supporting irrigation fluid bags and the like of a wide range of bag lengths and overall bag sizes wherein the apparatus includes a body member including a recess for supporting the bag and a semi-rigid harness-like support structure associated with the body for retaining bags of various lengths and overall sizes supported on the body from the bottom portion of the bag, rather than hanging the bag, to provide access to the bag discharge ports or conduits.

In accordance with another aspect of the invention, a container support body of the apparatus, and associated support or retaining structure are arranged to support fluid filled containers or bags inclined from the vertical in a working position of the apparatus to more securely retain the fluid container in its working position when an apparatus cover or door is opened with respect to the support body.

In accordance with another aspect of the present invention an apparatus for supporting and discharging flexible fluid containers includes an inflatable bladder which applies uniform pressure to a fluid container, such as a conventional medical irrigation fluid bag, and is adapted to be disconnected from a source of pressurizing fluid in the event that the bladder is energized when the door or closure is open to prevent catastrophic high pressure forces from being exerted on the bladder and on a fluid container or bag.

Still further, the present invention provides an apparatus for supporting and discharging flexible medical irrigation fluid containers and the like which includes a control circuit including a bladder pressure air fill and exhaust valve which is operable to exhaust pressure air from the bladder rapidly, even at relatively low pressure conditions when the apparatus is deenergized. The control system also includes push button control valves which are easily operated and a pressure regulator valve which is easily controlled to adjust the fluid container squeeze pressure.

Those skilled in the art will further appreciate the above mentioned features and advantages of the invention together with other superior aspects thereof upon reading the detailed description which follows in conjunction with the drawings.

DETAILED DESCRIPTION OF PREFERRED EMBODIMENTS

Figure 1:
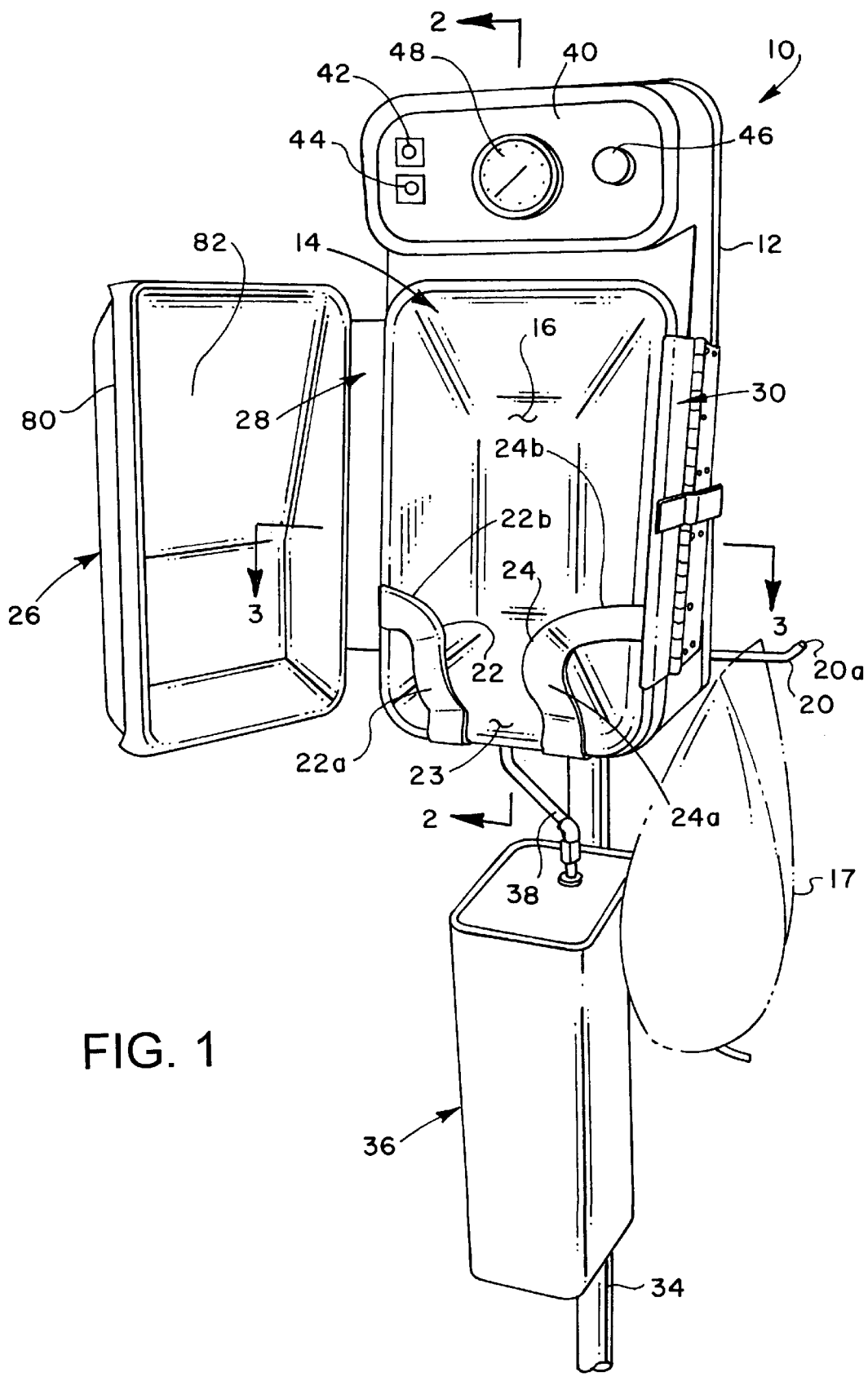
FIG. 1 is a perspective view of an apparatus for supporting and discharging flexible fluid containers in accordance with the invention.

In the description which follows like elements are marked throughout the specification and drawing with the same reference numerals, respectively. The drawing figures are not necessarily to scale and certain features of the invention may be shown in generalized or schematic form in the interest of clarity and conciseness.

Referring to FIG. 1, an apparatus for supporting and discharging fluid from a flexible medical irrigation fluid container or bag is illustrated and generally designated by the numeral 10. The apparatus 10 comprises a molded, generally rectangular body 12 which supports an inflatable bladder 14 in a cavity or recess 16 for receiving a flexible fluid container or bag, such as a bag 17 containing irrigation fluid and shown hanging on a laterally projecting storage hanger rod 20 supported by the body 12. Opposed fluid bag support members or harness brackets 22 and 24 are supported on the body 12 at the lower end of recess 16 for retaining one of the aforementioned fluid containers or bags so that a bottom discharge conduit of the bag may project downwardly through a gap 23 between the brackets 22 and 24 for connection to further fluid conducting structure, not shown in FIG. 1.

A clear plastic, generally rectangular outline door or closure 26 is supported on the body 12 by a hinge 28 for movement between the open position shown in FIG. 1 to a closed position wherein the door is latched by a hinge and latch structure 30 suitably connected to the opposite side of the body 12, as shown.

The apparatus 10 is adapted to be disposed on a suitable tubular column type support 34 by structure to be described in further detail herein, which support may also provide for supporting a source of pressure fluid 36, such as compressed air, for operation of the apparatus 10. The source of pressure fluid 36 may comprise a small air pump or compressor driven by a suitable electric motor, neither shown, and connected to a discharge conduit 38 which is adapted to be connected to a control circuit for the apparatus 10, also to be described in further detail herein.

Referring further to FIG. 1, the apparatus 10 also includes a control panel 40 disposed on the body 12 above the door 26 and including respective manual push button control valves 42 and 44 for controlling inflation of the bladder 14 and deflation of the bladder 14, respectively. A manually operable and rotatable control knob 46 is disposed on panel 40 for setting a regulated pressure of pressure fluid acting to inflate the bladder 14. The control panel 40 may also include a pressure gauge 48 to indicate the pressure set and maintained in bladder 14 by the control circuit.

Figure 2:
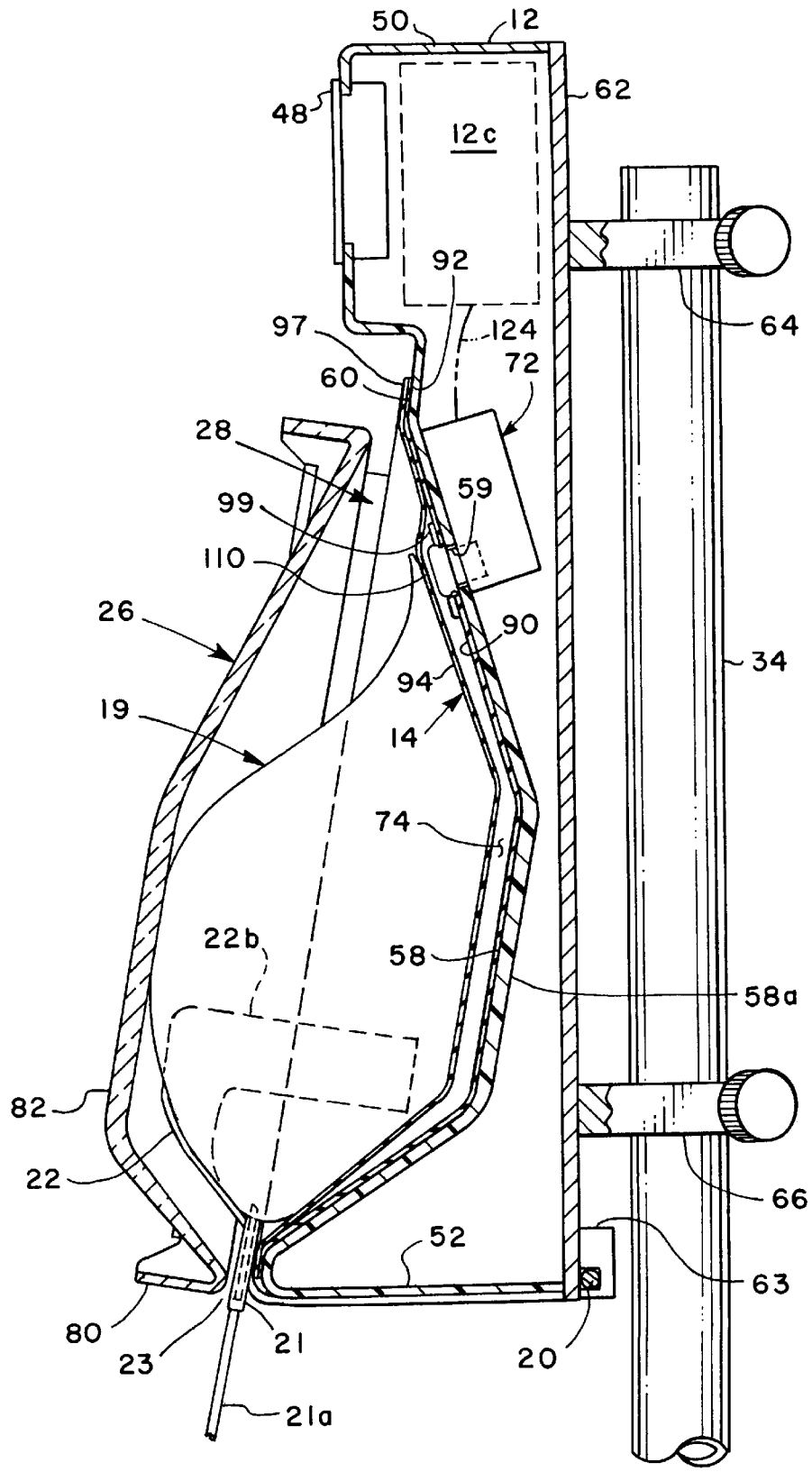
FIG. 2 is a central section view taken generally along the line 2—2 of FIG. 1.
Figure 3:
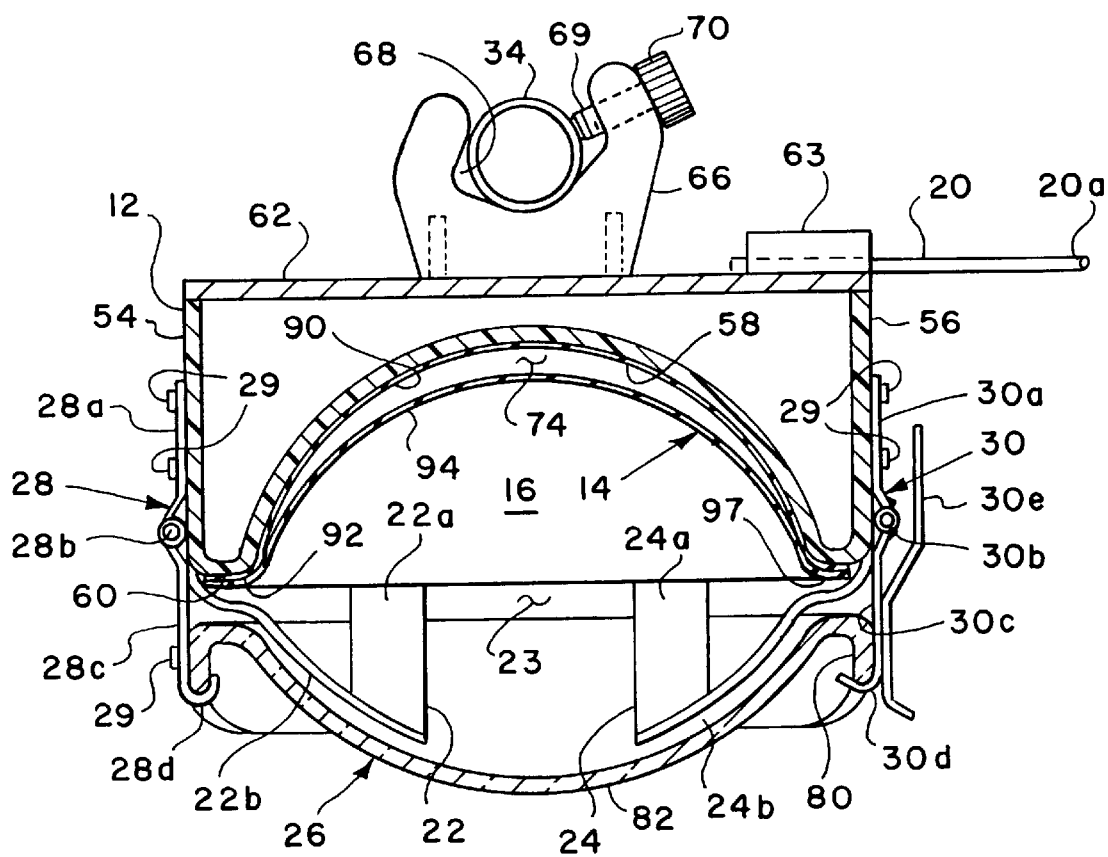
FIG. 3 is a section view taken generally along the line 3—3 of FIG. 1.

Referring now to FIGS. 2 and 3, wherein door 26 is shown in the closed position with a flexible bag type fluid filled container 19, not shown in FIG. 3, disposed in recess 16, the body 12 preferably comprises a molded plastic shell having a top wall 50, a bottom wall 52, FIG. 2, opposed side walls 54 and 56, FIG. 3, and a front wall 58 which is concavely contoured to provide the recess 16. The recess 16 is also delimited by a perimeter planar wall surface 60 for supporting a peripheral edge of the bladder 14 which, in FIGS. 2 and 3, is shown partially inflated to apply substantially uniform pressure to the flexible bag type fluid container 19 disposed in the recess 16. The container 19 includes one or more discharge ports or conduits 21, one shown, extending downward from the lower end of the recess 16 through gap 23, as shown in FIG. 2.

A generally rectangular, planar, back cover 62 is suitably removably connected to the body 12 by mechanical fasteners, not shown, and supports spaced apart mounting brackets 64 and 66 for supporting the apparatus 10 on the column member 34. As shown in FIG. 3, the support bracket 66 includes a contoured recess 68 for receiving the cylindrical cross section column member 34 and wherein the bracket 66 may be secured to the column member by a setscrew 69 having a manually operated adjustment knob 70 secured thereto for adjusting and holding a position of the apparatus 10 on the column member 34. The bracket 64 is preferably substantially like the bracket 66 and is secured to the column member 34 in the same manner.

As further shown FIGS. 2 and 3, the retractable bag hanger 20 comprises an elongated rod which is secured to the back cover or panel 62 by a support bracket 63 and whereby the hanger 20 may be extended to the working position shown in FIG. 3 or retracted by pushing the distal end 20a of the hanger toward the side wall 56. In this regard the bracket 63 supports the hanger 20 for slidable movement between the position shown and a retracted position.

Referring again to FIG. 2, the wall 58 of the body 12 includes a bore 59 formed therein for connection to a quick opening bladder fill and exhaust valve, generally designated by the numeral 72. The valve 72 is operably connected to the bladder 14 to provide pressure fluid to expand a chamber 74 within the bladder to cause the bladder to forcibly expand and engage bag 19 which is squeezed between the bladder and the door 26 in the closed position of the door, as shown in FIGS. 2 and 3. The bag 19 is also, of course, restrained by the brackets 22 and 24 and the brackets 22 and 24 are suitably contoured to be disposed directly adjacent to the door 26 in its closed position and to support a fluid container, such as bag 19, generally at a lower portion thereof.

The door 26 also comprises a member which may be molded in one piece out of clear plastic, such as a polycarbonate. The door 26 includes a peripheral rectangular flange 80 and a recessed wall 82 which is contoured, as shown in FIGS. 2 and 3, to be closely adjacent to the harness brackets 22 and 24 in the door closed position while also being in proximity to the bag 19 for forcible restraining engagement therewith in response to displacement of the bladder 14.

As shown in FIG. 3, the door hinge 28 includes a first leaf 28a which is secured to body side wall 54 by suitable fasteners 29, as shown. A hinge pin 28b connects the elongated leaf 28a to an elongated hinge leaf 28c. Leaf 28c includes a distal end 28d which is folded or turned about 180 degrees, as shown, to provide a slot for engagement with an edge of a part of the peripheral flange 80 of the door 26, as shown. The leaf 28c is also secured to the door 26, by suitable spaced apart fasteners 29, one shown in FIG. 3.

Referring further to FIG. 3, the hinge and latch structure 30 includes a first elongated leaf 30a which is secured to the side wall 56 by suitable fasteners 29 and to a hinge pin 30b which secures the leaf 30a to a latch leaf 30c having a hook shaped distal end 30d providing a slot for engagement with a portion of the peripheral flange 80, as shown in FIG. 3, to retain the door in the closed position. The latch leaf 30c may be biased to rotate in a clockwise direction about the axis of the hinge pin 30b, viewing FIG. 3, by suitable torsion springs, not shown. A release handle 30e is secured to the leaf 30c for rotating the leaf in the opposite direction to disengage it from the flange 80 of the door 26 to allow the door to be opened.

One important aspect of the apparatus 10 of the present invention pertains to the inclination of the peripheral wall 60 and at least a wall portion 58a, FIG. 2, of the recessed wall 58 of the body 12 so that a container, such as the container 19, will tend to reside in engagement with the wall 58 and not tend to fall out of the recess 16 when the door 26 is opened. Peripheral wall 60 and wall portion 58a are preferably parallel and inclined to the vertical at an angle of about 10°. Another important feature of the invention, as set forth above, pertains to the arrangement of the brackets 22 and 24 which provide for retaining a bag, such as the bag 19, in the recess 16 when the door 26 is open. The opposed brackets 22 and 24 also provide for supporting various lengths and overall sizes of flexible fluid containers or bags in the recess 16 for disposition of bag discharge ports or conduits, such as the conduit 21, from the lower end of the apparatus 10 and through the gap 23 between the brackets, as shown in FIG. 2. In this regard, of course, the door 26 is supported in a stand-off position from the peripheral wall 60 when the door is closed, as shown in FIGS. 2 and 3, while also providing suitable support for a fluid container when the bladder 14 is inflated by pressure air in the chamber 74. In particular, the brackets 22 and 24 are provided with contoured, generally vertically extending leg portions 22a and 24a which merge into generally horizontally extending leg portions 22b and 24b and are contoured to essentially be contiguous with the wall 82 of the door 26 when the door is in the closed and working position. In this way, the door 26 and the harness brackets 22 and 24 support the fluid container for projection of its discharge ports or conduits through the gap 23 for a wide range of sizes of fluid containers. Moreover, the door 26 and the brackets 22 and 24 support the container when the bladder 14 is pressurizing the container or "squeezing" the container to discharge fluids therefrom.

Figure 5:
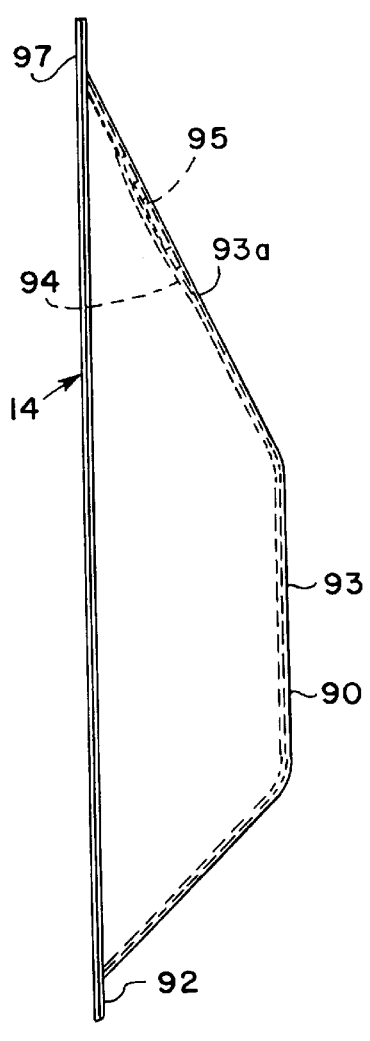
FIG. 5 is a side elevation of the fluid container squeeze bladder of the apparatus.
Figure 6:
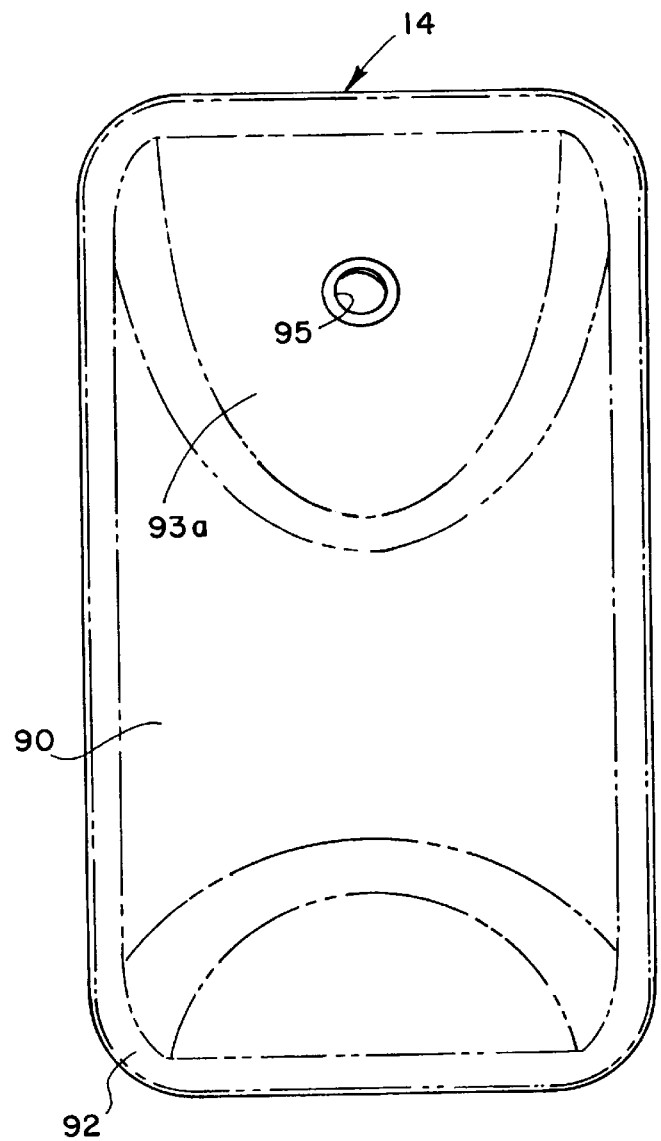
FIG. 6 is a rear elevation of the fluid container squeeze bladder.

Referring now briefly to FIGS. 5 and 6, the configuration of the inflatable bladder 14 is illustrated. The bladder 14 includes a contoured panel or back part 90 which is generally rectangular in shape and is formed with a perimeter flange 92 which is substantially planar. A recessed wall 93 is relieved away from the plane of the flange 92 and has substantially the same contour or shape as the recess 16 defined by wall 58 of the body 12. The flange 92 is adapted to engage the perimeter wall 60 of the body 12. The back part 90 includes an opening 95 formed in an upper sloped section 93a of the wall 93, as shown in FIGS. 5 and 6, for a purpose to be described hereinbelow.

As shown in FIGS. 2, 3 and 5, the bladder 14 includes a flexible displaceable part 94 having substantially the same shape as the part 90. The part 94 is formed of a suitable flexible elastomer or polymer material and is secured in sealing engagement with the part 90 at a perimeter flange 97 thereof corresponding to the perimeter flange 92. Accordingly, the chamber 74 is formed between the bladder parts 90 and 94 such that when pressure fluid, such as compressed air, is introduced into the chamber 74 through the opening 95 and with the bladder 14 disposed in the recess 16 on the body 12, the displaceable part 94 will engage the fluid container 19 substantially uniformly over a surface of the container facing the bladder to effect a squeezing action between the bladder 14 and the door 26. The shape of the bladder panel or wall parts 90 and 94 may be provided by molding these parts from a flexible material, such as urethane, and adhesively or RF bonding the parts together at the perimeter flanges 92 and 97 to form the bladder 14. The bladder 14 is secured in recess 16 in a manner as described below in conjunction with FIGS. 4A and 4B.

Figures 4A, 4B:
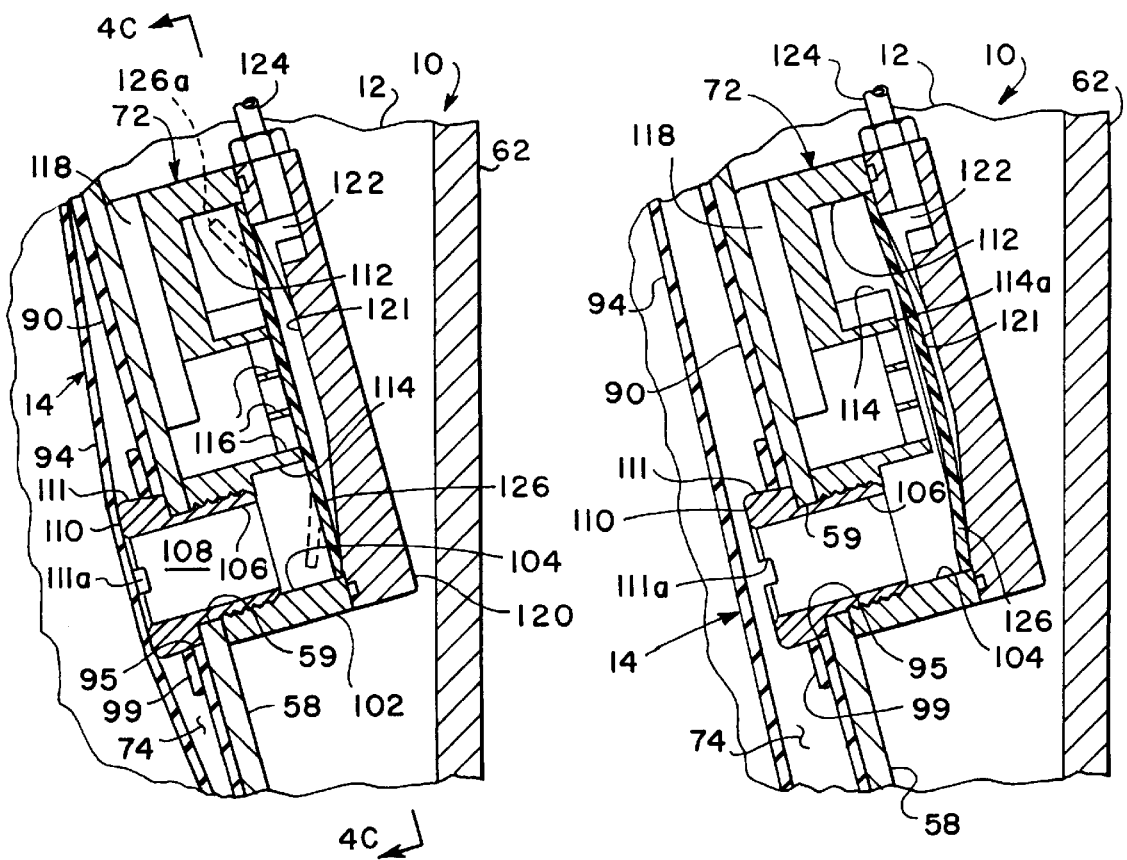
FIGS. 4A and 4B are central section views taken in the same plane as FIG. 2 and through a pressure air fill and low pressure rapid exhaust valve, showing its connection to the inflatable container squeeze bladder.

Referring to FIG. 4A, the bladder 14 is shown in section view wherein the opening 95 in the part 90 is reinforced by a generally cylindrical flat ring grommet 99 which is suitably bonded to the part 90 and further defines the opening 95. The grommet 99 is preferably formed of resilient material, such as synthetic rubber. As also shown in FIG. 4A, the valve 72 comprises a generally rectangular body member 102 having a fluid transfer port 104 formed therein. The body member 102 is adapted to be secured to the wall 58 at opening 59 therein by a threaded plug member 106 which includes a tubular bore 108 formed therein and a generally cylindrical head 110 with an outer, peripheral generally cylindrical wall surface having a somewhat reentrant contour as indicated at 111. In this way the grommet 99 may be elastically stretched and forcibly slipped over the head 110 and retained thereon in fluid tight engagement therewith, as shown, with the bladder part 90 substantially flush with surface of the wall 58.

Figure 4C:
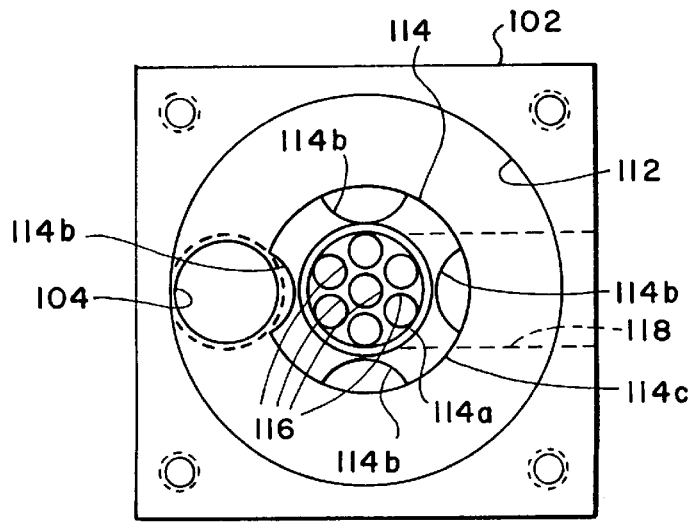
FIG. 4C is a view of the valve body taken generally from line 4C—4C of FIG. 4A.

Opposed slots 111a, one shown, are formed in the head 110 and intersect the wall 111 and the bore 108. Accordingly, if the bladder part 94 is in engagement with the head 110, as shown in FIG. 4A, pressure fluid may still flow between the chamber 74 and the bore 108 through the slots 111a. Referring also to FIG. 4C, the valve body 102 is formed with an annular channel 112 and a substantially centered boss 114 with plural passageways 116 formed therein and which are in communication with a lateral passage 118 opening to the exterior of the valve 72. Pressure air in chamber 74 may be vented via the bore 108, the channel 112 and the passages 116 and 118. The boss 114 has an annular closure seat surface 114a and circumferentially spaced flow passages 114b adjacent to the seat surface and formed in the outer wall 114c of the boss.

As further shown in FIGS. 4A and 4B, the valve 72 includes a generally rectangular cover member 120 adapted to be releasably secured to valve body 102 in fluid tight engagement by suitable fasteners, not shown. The cover member 120 includes a laterally projecting pressure fluid inlet port 122 formed therein and adapted to be connected to a suitable pressure fluid conduit 124 comprising part of a control circuit for the apparatus 10 and which is described hereinbelow. The cover member 120 also includes a relatively shallow cylindrical dish shaped recess 121 formed in a surface which faces valve body 102. A generally cylindrical, flexible, thin walled disc closure member 126 is retained between the valve cover 120 and the valve body 102, as shown in FIGS. 4A and 4B. In the condition of the valve 72 shown in FIG. 4A, the closure member 126 is engaged with seat surface 114a to close over the passages 116 to prevent pressure fluid from escaping the chamber 74. In the position of the closure member 126 shown in FIG. 4A, no unbalanced pressure fluid forces are acting on either side of the closure member.

However, in response to pressure fluid being introduced to the port 122 and recess 121 by way of the conduit 124, the peripheral edge 126a of the closure member 126 will be displaced into the channel 112 wherein sufficient clearance will be provided around the edge 126a, as shown by the alternate position lines in FIG. 4A, to allow pressure fluid to flow rapidly into the channel 112 through the port 104 and bore 108 and into the chamber 74 to inflate the bladder 14 and displace the bladder part 94 into forcible engagement with fluid container 19, for example. In response to venting of pressure fluid from the recess 121 and the port 122, pressure fluid in the annular channel 112 from chamber 74 will act on the disc shaped closure member 126 to displace it away from surface 114a to the position shown in FIG. 4B to allow pressure fluid to flow rapidly from the chamber 74 through the bore 108, port 104 and the channel 112 and between the closure 126 and the boss 114 to vent through passages 116, 118.

Thanks to the configuration of the valve 72, including the lightweight flexible disc-shaped closure member 126 and the configurations of the valve body 102 and cover 120, the valve is operable to vent the chamber 74 quickly, even when the chamber is inflated at relatively low pressures, in the range of 100 mm Hg or less, while at same time the valve 72 is operable to also supply fluid to and vent fluid from the chamber 74 rapidly at higher pressures up to a typical maximum working pressure of the apparatus 10 of about 1000 mm Hg, for example. The closure member 126 will also assume the position shown in FIG. 4A when a balanced pressure force exists on the closure member as a result of the pressure of the source of fluid to the port 122 and the recess 121 and the pressure of fluid in the chamber 74.

Figure 7:
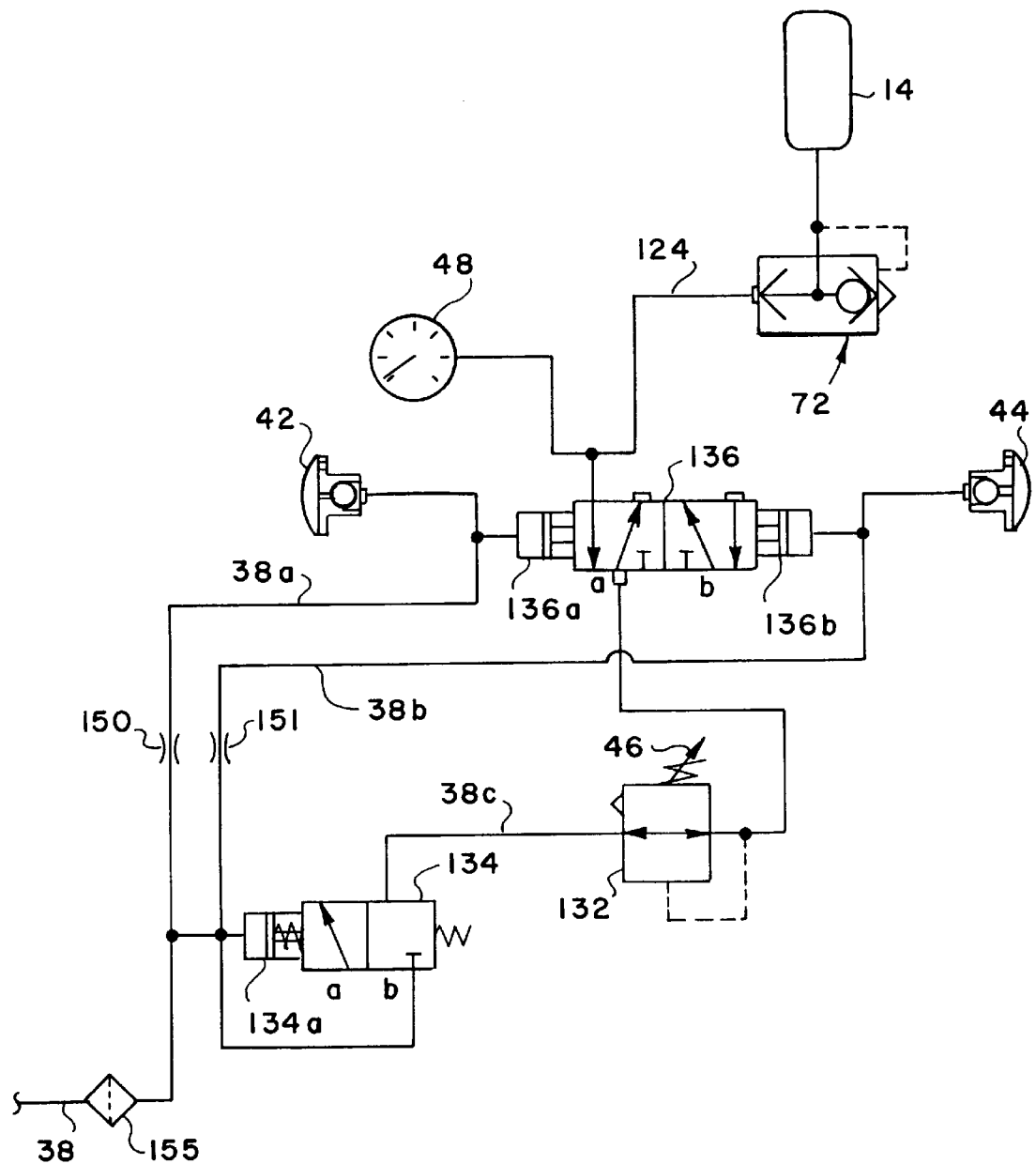
FIG. 7 is a schematic diagram of a control system for the apparatus of the present invention.

Referring now to FIG. 7, there is illustrated a control circuit for the apparatus 10 which is adapted to receive pressure air by way of the conduit 38 and includes the aforementioned momentary push button valves 42 and 44, the valve 72, a pressure regulator 132 operably connected to the adjustment knob 46 and in circuit with a pilot actuated, spring return, two position priority valve 134 having a pilot actuator 134a for receiving pressure fluid to place the valve in the position a, as shown. The valve 134 is spring biased into the position b. The control circuit shown in FIG. 7 also includes a two position valve 136 which is operated by pilot actuators 136a and 136b to be in the respective a and b positions shown. The valve 136 is operably connected to the momentary push button valves 42 and 44, also as shown. The valves 42 and 44 include, respectively, closure members 42a and 44a and flexible membrane pushbuttons 42b and 44b which unseat the respective closure members when actuated. Valves 42 and 44 may be of a type described in U.S. Pat. No. 5,425,529 issued to Joe E. West on Jun. 20, 1995. The subject matter of U.S. Pat. No. 5,425,529 is incorporated herein by reference. Momentary valve 42 and pilot actuator 136a are connected to the source of pressure fluid including the conduit 38 by way of a conduit 38a having a suitable flow restrictor or orifice 150 disposed therein. Pressure air is also supplied by way of conduit 38b and orifice 151 disposed therein to the pilot actuator 136b and to the momentary manually actuated push button valve 44. Pressure air is supplied by valve 136 to bladder 14 by way of valve 72 through conduit 124. Pressure gauge 48 is also connected to conduit 124 to provide a readout of regulated pressure in the bladder 14. Flow restricting orifice 151 is interposed in conduit 38b between its connection to conduit 38a at valve 134 and the pilot actuator 136b.

Valve 134 is adapted to supply pressure air to the regulator 132 and the bladder 14 via conduit 38c only when a minimum pressure is available in supply conduit 38, 38a. If the pressure in conduit 38, 38a drops below a predetermined minimum, about 3.0 psig, for example, valve 134 shifts to the position b so that pressure air is supplied only to the valves 42 and 44 to assure that the valve 136 may be shifted to position b upon actuation of valve 44 to vent pressure air from the bladder 14.

In operation of the control system illustrated in FIG. 7, with adequate pressure air supplied through conduit 38 and filter 155 to conduits 38a and 38b, valve 136 will remain in whichever position it has been previously set, since the pilot actuators 136a and 136b are balanced actuators. If pressure air is sufficient in conduit 38a valve 134 will shift to position a to supply pressure air to the regulator 132 which may be adjusted by the operating knob 46 to a predetermined pressure value indicated by suitable indicia on the control panel 40. When the pressure switch or valve 42 is actuated momentarily pressure air is vented from conduit 38a between the valve 42 and the orifice 150 to relieve pressure in pilot actuator 136a causing pilot actuator 136b to shift valve 136 to position b supplying pressure air to the bladder 14 by way of valve 72 at a regulated pressure which may now be read or verified by pressure gauge 48. The pressure in bladder 14 may, of course, be adjusted at will.

However, if the pressure in bladder 14 exceeds a predetermined amount with door 26 open a resultant pressure force acting on the bladder will cause it to disengage from the boss 110, due to the differential areas of the bladder parts 94 and 90 on which pressure air is acting. In this way, if the door 26 is opened when the bladder 14 is pressurized or vice versa, the bladder 14 will disengage from the source of pressure air and rapidly deflate to prevent rupturing the bladder. If the bladder 14 is over pressured with the door 26 closed, with or without a fluid container in recess 16, the bladder will elastically distend at the grommet 99 and allow pressure air to bleed out of chamber 74 between the grommet and boss 110. In this way the bladder 14 is normally protected from catastrophic failure due to an overpressure condition therein.

If valve 44 is actuated, pressure in conduit 38b drops momentarily allowing valve 136 to shift to position a under the urging of pilot actuator 136a relieving pressure acting on valve closure member 126 of valve 72 thereby venting the bladder 14. The components of the control circuit shown in FIG. 7 and described above but not otherwise accounted for may be disposed in a cavity 12c, FIG. 2, of body 12.

The operation of the apparatus 10 is believed to be understandable to one of ordinary skill in the art from the foregoing description. However, briefly, to begin use of the apparatus 10 the door 26 is moved to the open position shown in FIG. 1 and, with the bladder 14 deflated, a fluid container, such as the container 19, is placed in the cavity or recess 16 and supported by the brackets 22 and 24 with a discharge conduit 21 extending between the brackets downwardly past the lower or bottom wall 52 of the body 12. The door 26 may then be closed and latched by the latch member 30c which may be momentarily deflected by an edge of the peripheral flange 80 of the door as the flange engages the distal end 30d of the latch and moves past the distal end to the position of the door as shown in FIG. 3. With the bag 19 in place and the door 26 closed the "on" push button valve 42 may be actuated momentarily to pressurize bladder 14 and the desired working pressure set by the adjustment knob 46 while reading the set pressure at gauge 48 whereupon pressure air will be supplied to the bladder 14 to inflate the bladder and forcibly engage the bag or container 19 to begin squeezing the container to discharge fluid therefrom at a regulated pressure, which pressure may be adjusted at will.

When it is desired to change the fluid container or bag, after deflating bladder 14 by pressing push button valve 44, the door 26 is opened by depressing the distal end of latch handle 30e toward the body side wall 56 to rotate the latch leaf 30c out of engagement with the door so that the door may be swung to the open position shown in FIG. 1. However, the container 19 is in no danger of falling out of the recess 16 due to the inclination of the recess from the vertical (about 10° is preferred) and the provision of the harness brackets 22 and 24. The container 19 may be easily replaced by a container of a selected size over a relatively wide range of sizes, again thanks to the configuration of the container recess 16, the harness brackets 22 and 24, and the door 26.

The apparatus 10 may be manufactured of conventional engineering materials used for similar apparatus. The body 12 may be formed of molded plastic, such an ABS polymer for example, as well as the brackets 22 and 24. The hinge assemblies 28 and 30 may be formed of a suitable engineering material, such as stainless steel. Conventional engineering materials used for medical equipment may be used for the other components described herein.

Although a preferred embodiment of the invention has been described in detail herein, those skilled in the art will recognize that various substitutions and modifications may be made to the apparatus without departing from the scope and spirit of the appended claims.

What is claimed is:

1. An apparatus for supporting and effecting discharge of fluid from a flexible fluid container, such as a medical irrigation fluid bag, said apparatus comprising:

a body including a recess formed therein for receiving a flexible fluid container, said recess being delimited by a wall portion of said body;

a support connected to said body and engageable with a lower portion of a flexible fluid container for supporting said fluid container in said recess;

a door connected to said body and being movable between an open position for inserting and removing said fluid container with respect to said recess and a closed position for retaining said fluid container in said recess;

said wall portion of said body is inclined upwardly from said support in a direction away from said door to provide a support surface for said fluid container to minimize the risk of said fluid container tilting out of said recess when said door is in an open position; and an inflatable bladder disposed in said recess between said fluid container and said wall portion and connected to a source of pressure fluid for undergoing inflation to forcibly engage said fluid container to urge discharge of fluid therefrom.

2. The apparatus set forth in claim 1 wherein:

said bladder includes an inflation chamber and a part defining an opening in said bladder for engagement with a member disposed on said body for supplying pressure fluid to said inflation chamber.

3. The apparatus set forth in claim 2 wherein:

said member includes a pressure fluid passage therein for supplying pressure fluid to said bladder.

4. An apparatus for supporting and effecting discharge of fluid from a flexible fluid container, such as a medical irrigation fluid bag, said apparatus comprising:

a body including a recess formed therein for receiving a flexible fluid container, said recess being delimited by a wall portion of said body;

a support connected to said body for supporting a flexible fluid container in said recess by a lower portion of said fluid container, said support comprising opposed support brackets connected to said body and engageable with said fluid container to retain said fluid container in said recess;

a door connected to said body and being movable between an open position for inserting and removing said fluid container with respect to said recess and a closed position for retaining said fluid container in said recess; and an inflatable bladder disposed in said recess between said fluid container and said wall portion and connected to a source of pressure fluid for undergoing inflation to forcibly engage said fluid container to urge discharge of fluid therefrom.

5. The apparatus set forth in claim 2 wherein:

said brackets are spaced apart on said body to provide a gap between said brackets and between said body and said door in the closed position thereof for extension of a fluid discharge conduit of said fluid container to the exterior of said apparatus.

6. An apparatus for supporting and effecting discharge of fluid from a flexible fluid container, such as a medical irrigation fluid bag, said apparatus comprising:

a body including a recess formed therein for receiving a flexible fluid container, said recess being delimited by a wall portion of said body;

a support connected to said body for supporting a flexible fluid container in said recess by a lower portion of said fluid container;

a door connected to said body and being movable between an open position for inserting and removing said fluid container with respect to said recess and a closed position for retaining said fluid container in said recess; and an inflatable bladder disposed in said recess between said fluid container and said wall portion and connected to a source of pressure air for undergoing inflation to forcibly engage said fluid container to urge discharge of fluid therefrom, said bladder including an inflation chamber and a part defining an opening in said bladder for engagement with a member disposed on said body for supplying pressure fluid to said inflation chamber, said opening in said bladder is defined by a resilient grommet which is forcibly engageable with said member disposed on said body and disengageable therefrom in response to a predetermined pressure in said inflation chamber when said door is in an open position.

7. An apparatus for supporting and effecting discharge of fluid from a flexible fluid container, such as a medical irrigation fluid bag, said apparatus comprising:

a body including a recess formed therein for receiving a flexible fluid container, said recess being delimited by a wall portion of said body;

a support connected to said body for supporting a flexible fluid container in said recess by a lower portion of said fluid container;

a door connected to said body and being movable between an open position for inserting and removing said fluid container with respect to said recess and a closed position for retaining said fluid container in said recess;

an inflatable bladder disposed in said recess between said fluid container and said wall portion and connected to a source of pressure fluid for undergoing inflation to forcibly engage said fluid container to urge discharge of fluid therefrom, said bladder including an inflation chamber and a part defining an opening in said bladder for engagement with a member disposed on said body for supplying pressure fluid to said inflation chamber; and a control circuit in communication with said member on said body for supplying pressure fluid to said bladder, said control circuit including a conduit connected to a source of pressure fluid and to a fluid supply and an exhaust valve interposed said member on said body and said source of pressure fluid and operable to rapidly deflate said bladder by exhausting pressure fluid from said inflation chamber in response to a signal from said control circuit.

8. The apparatus set forth in claim 7 wherein:

said control circuit includes a control valve movable between a first position for supplying pressure fluid to said bladder by way of said exhaust valve and a second position to vent pressure fluid from said exhaust valve to provide operation of said exhaust valve to rapidly vent pressure fluid from said bladder.

9. The apparatus set forth in claim 8 including:

momentary on and off valves operably connected to said control valve for shifting said control valve between said position for supplying pressure fluid to said bladder and said position venting pressure fluid from said exhaust valve.

10. The apparatus set forth in claim 8 including:
a pressure regulator valve in said control circuit between said source of pressure fluid and said control valve for selectively regulating the pressure of fluid conducted to said bladder.

11. The apparatus set forth in claim 10 including:
a priority valve operable to prevent flow of pressure fluid to said pressure regulator when pressure fluid in said supply conduit is less than a predetermined minimum pressure so as to provide sufficient pressure fluid to said on and off valves to enable said on and off valves to effect operation of said control valve.

12. The apparatus set forth in claim 8 wherein:
said exhaust valve includes a valve body member including a flow port formed therein in communication with said member connected to said bladder for conducting pressure fluid to and from said inflation chamber, an exhaust port formed in said valve body member and a flexible disc closure member operable to be moved to a position to close over said exhaust port to prevent venting pressure fluid from said inflation chamber in response to pressure fluid acting on said closure member, and said closure member being responsive to venting of pressure fluid acting thereon to move to a second position to uncover said exhaust port and provide rapid venting of pressure fluid from said inflation chamber.

13. The apparatus set forth in claim 12 wherein:
said exhaust valve includes a cover connected to said body member and defining a recess for pressure fluid to act on said closure member to deflect said closure member to a position to cause pressure fluid to flow from said control valve to said inflation chamber.

14. The apparatus set forth in claim 13 wherein:
said body member of said exhaust valve includes a boss formed therein and defining said exhaust port, a channel formed around said boss and in communication with said flow port and a fluid supply port in said cover for conducting pressure fluid to said inflation chamber in response to deflection of said closure member into said channel.

15. An apparatus for supporting a flexible fluid container wherein said container includes at least one discharge conduit disposed at a bottom side of said container, said apparatus comprising:
a body including a recess formed therein for receiving a flexible fluid container, said recess being delimited by a wall portion of said body inclined to the vertical;
opposed support brackets connected to said body and engageable with said fluid container to retain said fluid container in said recess, said brackets being spaced apart to provide a gap therebetween for extension of a fluid discharge conduit of said container to the exterior of said apparatus;
a door connected to said body and being movable between an open position for inserting and removing said fluid container with respect to said recess and a closed position for retaining said fluid container in said recess; and
a member disposed in said recess and operable to forcibly engage said fluid container to urge discharge of fluid therefrom.

16. The apparatus set forth in claim 15 wherein:
said brackets are spaced apart on said body to provide a gap between said brackets and between said body and said door in the closed position thereof for extension of a fluid discharge conduit of said fluid container to the exterior of said apparatus.

17. An apparatus for supporting and effecting discharge of fluid from a flexible fluid container, comprising:
a body including a recess formed therein for receiving a flexible fluid container, said recess being delimited by a wall portion of said body;
an inflatable bladder disposed in said recess between said fluid container and said wall portion;
a member mounted on said wall portion and engageable with said bladder for supplying pressure fluid to an inflation chamber of said bladder and venting pressure fluid from said inflation chamber, said member and said bladder being cooperable to provide for disengagement of said bladder from said member at a predetermined pressure in said inflation chamber to prevent at least one of an overpressure condition in said inflation chamber and an excessive pressure force acting on said fluid container by said bladder.

18. The apparatus set forth in claim 17 wherein:
said bladder includes an opening in a part of said bladder and a resilient grommet encircling said opening, and said member includes a head portion adapted to project through said opening and engageable with said grommet to retain said member connected to said bladder at a pressure condition in said inflation chamber less than said predetermined pressure.

19. The apparatus set forth in claim 17 including:
a control circuit in communication with said member on said body for supplying pressure fluid to said bladder, said control circuit including a conduit connected to a source of pressure fluid and to a fluid supply and exhaust valve interposed said member and said source of pressure fluid and operable to rapidly deflate said bladder by exhausting pressure fluid from said inflation chamber in response to a pressure fluid signal from said control circuit.

20. The apparatus set forth in claim 19 wherein:
said control circuit includes a control valve movable between a first position for supplying pressure fluid to said bladder by way of said exhaust valve and a second position to vent pressure fluid between said control valve and said exhaust valve to provide operation of said exhaust valve to rapidly vent pressure fluid from said bladder.

21. An apparatus for supporting and effecting discharge of fluid from a flexible fluid container comprising:
a body for supporting said fluid container;
a pressure fluid actuated member supported on said body for effecting squeezing action on said fluid container to pressurize fluid in said container and force discharge of fluid from said container; and
a control circuit for controlling operation of said member to effect squeezing and to relieve squeezing of said fluid container, said control circuit including a valve for supplying pressure fluid to said member and for rapidly exhausting pressure fluid from said member, said valve including a valve body member including a transfer port formed therein for communication with said member to supply pressure fluid to effect squeezing of said fluid container, an exhaust port formed in said valve body member and a flexible disc closure member operable to be moved to a position to close over said exhaust port to prevent venting pressure fluid in response to pressure fluid acting on said closure member, and said closure member being responsive to venting of pressure fluid acting thereon to move to a second position to uncover said exhaust port to provide rapid venting of pressure fluid from said member.

22. The apparatus set forth in claim 21 wherein:

said valve body member includes a boss formed therein defining said exhaust port, a channel formed around said boss and in communication with said transfer port and a fluid supply port in a cover connected to said valve body member for conducting pressure fluid to said inflation chamber in response to deflection of said closure member into said channel.

23. The apparatus set forth in claim 22 wherein:

said boss includes an annular seat surface engageable with said closure member.

24. An apparatus for supporting and effecting discharge of fluid from a flexible fluid container, such as a medical irrigation fluid bag, said apparatus comprising:

a body including a recess formed therein for receiving a flexible fluid container, said recess being delimited by a wall portion of said body;

a support connected to said body for supporting a flexible fluid container in said recess by a lower portion of said fluid container;

a door connected to said body and being movable between an open position for inserting and removing said fluid container with respect to said recess and a closed position for retaining said fluid container in said recess; and an inflatable bladder disposed in said recess between said fluid container and said wall portion and connected to a source of pressure air for undergoing inflation to forcibly engage said fluid container to urge discharge of fluid therefrom, said bladder including first and second parts, each including a peripheral flange, said flanges are joined together to form said inflation chamber between said first and second parts and said first and second parts are formed in a shape substantially conforming to the shape of said recess in said body and said first part is engageable with said wall portion of said body to act in supportive relationship to said fluid container when said fluid container is placed in said recess.

* * * * *